(12) United States Patent
Eagle et al.

(10) Patent No.: US 10,293,118 B2
(45) Date of Patent: May 21, 2019

(54) APPARATUS AND METHODS FOR MEASURING PERIPHERAL VENOUS PRESSURE AND APPLICATIONS OF SAME

(75) Inventors: Susan Eagle, Nashville, TN (US); Kevin Sexton, Nashville, TN (US); Colleen Brophy, Nashville, TN (US); Kyle Mitchell Hocking, Nashville, TN (US)

(73) Assignee: VANDERBILT UNIVERSITY, Nashville, TN (US)

(*) Notice: Subject to any disclaimer, the term of this patent is extended or adjusted under 35 U.S.C. 154(b) by 1062 days.

(21) Appl. No.: 14/232,571

(22) PCT Filed: Jul. 13, 2012

(86) PCT No.: PCT/US2012/046670
§ 371 (c)(1),
(2), (4) Date: Mar. 24, 2014

(87) PCT Pub. No.: WO2013/012721
PCT Pub. Date: Jan. 24, 2013

(65) Prior Publication Data
US 2014/0207062 A1    Jul. 24, 2014

Related U.S. Application Data

(60) Provisional application No. 61/508,523, filed on Jul. 15, 2011.

(51) Int. Cl.
*A61M 5/46* (2006.01)
*A61M 5/50* (2006.01)
(Continued)

(52) U.S. Cl.
CPC ....... *A61M 5/5086* (2013.01); *A61B 5/02141* (2013.01); *A61B 5/02152* (2013.01); *A61B 2560/0266* (2013.01)

(58) Field of Classification Search
CPC ............... A61B 5/02152; A61M 5/16859
See application file for complete search history.

(56) References Cited

U.S. PATENT DOCUMENTS 3,724,274 A    4/1973    Millar
3,738,356 A    6/1973    Workman
(Continued)

FOREIGN PATENT DOCUMENTS

WO    2003001973 A2    9/2003
WO    2010045556 A2    4/2010
WO    2010063676 A1    6/2010

OTHER PUBLICATIONS

Engineers Daily, Orifice Meter, 2011, Web, Retrieved from: https://web.archive.org/web/20110116092237/http://www.engineersdaily.com/2010/12/orificemeter.html.*
(Continued)

*Primary Examiner* — Sean P Dougherty
*Assistant Examiner* — Jairo H Portillo
(74) *Attorney, Agent, or Firm* — Locke Lord LLP; Tim Tingkang Xia, Esq.

(57) ABSTRACT

In one aspect, an apparatus for measuring peripheral venous pressure includes a tubing having two ends with one end connectable to a fluid source and the other end connectable to a vein, a fluid controlling device configured to have an on position and an off position, and at least one pressure sensor configured to measure fluid pressures therein. When the fluid controlling device is in the on position, fluid flow in the tubing is allowed to pass through the fluid controlling device, such that the at least one pressure sensor measures both a fluid pressure from the fluid source and a distal venous pressure from the vein. When the fluid controlling device is in the off position, no fluid flow in the tubing is allowed to pass through the fluid controlling device, such (Continued)

that the at least one pressure sensor measures the distal venous pressure from the vein only.

7 Claims, 6 Drawing Sheets

(51) Int. Cl.
*A61B 5/021* (2006.01)
*A61B 5/0215* (2006.01)

(56) References Cited

U.S. PATENT DOCUMENTS

| | | | |
|---|---|---|---|
| 3,980,082 A | 9/1976 | Miller | |
| 4,072,146 A | 2/1978 | Howes | |
| RE31,873 E | 4/1985 | Howes | |
| 4,530,696 A * | 7/1985 | Bisera | A61M 5/16859 128/DIG. 13 |
| 4,534,756 A * | 8/1985 | Nelson | A61M 5/365 604/505 |
| 5,078,687 A * | 1/1992 | Egolf | A61M 25/0606 604/164.02 |
| 5,423,743 A * | 6/1995 | Butterfield | A61M 5/16859 128/DIG. 13 |
| 5,643,302 A | 7/1997 | Beiser et al. | |
| 6,623,470 B2 | 9/2003 | Munis et al. | |
| 7,540,851 B2 | 6/2009 | O'Mahony et al. | |
| 7,826,890 B1 * | 11/2010 | Winchester, Jr. | A61B 5/0059 600/407 |
| 7,927,270 B2 | 4/2011 | Dlugos et al. | |
| 2003/0004492 A1 * | 1/2003 | Munis | A61B 5/021 604/503 |
| 2003/0187360 A1 * | 10/2003 | Waner | A61B 5/0059 600/478 |
| 2006/0206054 A1 * | 9/2006 | Shekalim | A61M 5/1454 604/122 |
| 2008/0161723 A1 | 7/2008 | Keenan et al. | |
| 2009/0173166 A1 * | 7/2009 | Genosar | G01F 1/708 73/861.05 |
| 2010/0191128 A1 | 7/2010 | Shelley et al. | |
| 2011/0106466 A1 * | 5/2011 | Furmanski | A61M 1/3653 702/51 |

OTHER PUBLICATIONS

Korean Intellectual Property Office (ISA/KR), "International Search Report", Korea, dated Jan. 17, 2013.
Becker, Lance et al.,The PULSE Initiative: Scientific Priorities and Strategic Planning for Resuscitation Research and Life Saving Therapies, Circulation 105:2562-2570, May 2002.
Convertino, Victor et al., Physiological and Medical Monitoring for En Route Care of Combat Casualties, The Journal of Trauma 64:S342-353, Apr. 2008.
Convertino, Victor et al., Identifying Physiological Measurements for Medical Monitoring: Implications For Autonomous Health Care in Austere Environments, Journal of Gravitational Physiology 14:P39-42, 2007.
Desebbe, Olivier et al., The Ability of Pleth Variability Index to Predict the Hemodynamic Effects of Positive End-Expiratory Pressure in Mechanically Ventilated Patients Under General Anesthesia, Anesthesia-Analgesia 110:792-798, Mar. 2010.
Amar, David et al., Correlation of Peripheral Venous Pressure and Central Venous Pressure in Surgical Patients, Journal of Cardiothoracic and Vascular Anesthesia 15:40-43, Feb. 2001.
Munis, James et al., Peripheral Venous Pressure as a Hemodynamic Variable in Neurosurgical Patients, Anesthesia-Analgesia 92:172-179, 2001.
Wolf, William et al., Cuff-occluded rate of rise of peripheral venous pressure: a new, highly sensitive technique for monitoring blood volume status during hemorrhage and resuscitation, Surgery 101:304-309, Mar. 1987.
Soller, Babs et al., Noninvasively determined muscle oxygen saturation is an early indicator of central hypovolemia in humans, Journal of Applied Physiology 104:475-481, Feb. 2008.

* cited by examiner

APPARATUS AND METHODS FOR MEASURING PERIPHERAL VENOUS PRESSURE AND APPLICATIONS OF SAME

CROSS-REFERENCE TO RELATED PATENT APPLICATION

This PCT application claims priority to and the benefit of U.S. provisional patent application Ser. No. 61/508,523, filed on Jul. 15, 2011, entitled "SYSTEM AND METHODS OF UTILIZING PERIPHERAL VENOUS PRESSURE AND APPLICATIONS OF SAME", by Susan Eagle, Kevin Sexton, Colleen Brophy and Kyle Mitchell Hocking, which is incorporated herein in its entirety by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

FIELD OF THE INVENTION

This invention relates generally to intravenous (IV) therapy, and more particularly to apparatus and methods for measuring peripheral venous pressure (PVP), and its application in monitoring intravascular placement of a peripheral IV catheter.

BACKGROUND OF THE INVENTION

Invasive hemodynamic monitoring is routinely used in medical environments, such as operating rooms and critical-care settings, for determining volume status and cardiac function in patients. Limitations of invasive monitoring include advanced training, cost, time constraints, and potential for infectious and vascular complications. Newer sophisticated non-invasive monitoring devices for earlier detection of intravascular volume changes using plethysmography and muscle oxygen saturation may be impractical and expensive. Lack of sensitivity of traditional monitoring has prompted researchers to look for alternative means to more accurately estimate intravascular volume status.

Peripheral venous pressure (PVP) is increasingly used in the assessment of intravascular volume status. PVP accurately reflects central venous pressure, particularly in the setting of acute hemorrhage (>1000 mL). A method for dynamic measurement of intravascular volume status is cuff-occluded rate of rise of peripheral venous pressure (CORRP). CORRP allows for earlier detection of acute hypovolemia compared to traditional monitoring in animal models. The challenge is how to measure absolute PVP and CORRP in a non-invasive manner rather accurately.

Further, while seemingly simple, proper intravascular placement of the intravenous (IV) catheter is mandatory for effective IV volume resuscitation and IV pharmacologic administration. Malpositioning or misplacing of IV catheters may occur at any time during hospitalization or when a patient is in a status under the potential need of IV volume resuscitation and/or IV pharmacologic administration. Ambulatory patients may inadvertently displace the catheter, often secured with tape; patients in the operating room setting often have their arms tucked in sheets, away from the operative field, precluding inspection of the IV insertion site for signs of infiltration; pediatric patients often have IV catheters secured with devices to prevent patient tampering—also obscuring the IV insertion site.

Malpositioning of a peripheral IV catheter into the extravascular space precludes the patient from receiving necessary resuscitative therapy. Fluid administration into subcutaneous tissue or fascia may result in compartment syndrome and loss of the extremity. Tissue necrosis and gangrene may result from tissue infiltration of vasoactive medications.

Therefore, a heretofore unaddressed need exists in the art to address the aforementioned deficiencies and inadequacies.

SUMMARY OF THE INVENTION

In one aspect of the present invention, an apparatus for measuring peripheral venous pressure (PVP) includes: a tubing having a first end and an opposite, second end, where the first end is connectable to a fluid source, and the second end is connectable to a vein, a fluid controlling device in fluid communication with the tubing, placed between the first and second ends of the tubing and configured to have an on position and an off position, a port device in fluid communication with the tubing, placed between the fluid controlling device and the second end of the tubing, at least one pressure sensor in fluid communication with the tubing through the port device, configured to measure fluid pressures therein, and a processor electrically coupled with the at least one pressure sensor for processing the measured fluid pressures by the at least one pressure sensor. In operation, when the fluid controlling device is in the on position, fluid flow in the tubing is allowed to pass through the fluid controlling device, such that the at least one pressure sensor measures both a fluid pressure from the fluid source and a distal venous pressure from the vein, and when the fluid controlling device is in the off position, no fluid flow in the tubing is allowed to pass through the fluid controlling device, such that the at least one pressure sensor measures the distal venous pressure from the vein only.

The fluid controlling device may be manually or automatically controllable. In one embodiment, the fluid controlling device includes a stopcock. In another embodiment, the fluid controlling device includes an intravascular line occlusion mechanism, which may be manual, automatic, or timed with cuff occlusion and cuff release.

In one embodiment, the port device includes a T-piece or Y-piece connector.

In one embodiment, the at least one pressure sensor includes a pressure transducer.

The processor in one embodiment is associated with a circuit board of data acquisition and process.

In one embodiment, the apparatus further includes a display in communication with the processor for displaying the processed fluid pressures. The display may include a graphic interface.

The apparatus in one embodiment further includes one or more additional port device in fluid communication with the tubing, placed between the fluid source and the port device or between the port device and the vein for measuring fluid pressures therein.

In one embodiment, the apparatus further includes an IV catheter for connecting the second end of the tubing to the vein.

In another aspect, the invention relates to an apparatus for measuring PVP. In one embodiment, the apparatus includes:

a tubing having a first end and an opposite, second end, where the first end is connectable to a fluid source, and the second end is connectable to a vein, a fluid controlling device in fluid communication with the tubing, placed between the first and second ends of the tubing and configured to have an on position and an off position, and at least one pressure sensor in fluid communication with the tubing, placed between the fluid controlling device and the second end of tubing and configured to measure fluid pressures therein. In operation, when the fluid controlling device is in the on position, fluid flow in the tubing is allowed to pass through the fluid controlling device, such that the at least one pressure sensor measures both a fluid pressure from the fluid source and a distal venous pressure from the vein, and when the fluid controlling device is in the off position, no fluid flow in the tubing is allowed to pass through the fluid controlling device, such that the at least one pressure sensor measures the distal venous pressure from the vein only.

The fluid controlling device may be manually or automatically controllable. In one embodiment, the fluid controlling device includes a stopcock. In another embodiment, the fluid controlling device includes an intravascular line occlusion mechanism, which may be manual, automatic, or timed with cuff occlusion and cuff release.

In one embodiment, the apparatus further includes a port device in fluid communication with the tubing, wherein the at least one pressure sensor is in fluid communication with the tubing through the port device. In a further embodiment, the port device includes a T-piece or Y-piece connector.

In one embodiment, the at least one pressure sensor includes a pressure transducer.

In one embodiment, the apparatus further includes a processor in communication with the at least one pressure sensor for processing the measured fluid pressures by the at least one pressure sensor.

In yet another aspect of the invention, a method of measuring PVP includes: providing a tubing operably connected between a fluid source and a vein, a fluid controlling device in fluid communication with the tubing, placed in the tubing and configured to have an on position and an off position, and at least one pressure sensor in fluid communication with the tubing, placed between the fluid controlling device and the vein, selectively passing fluid from the fluid source to the vein through the tubing by the fluid controlling device, measuring both a fluid pressure from the fluid source and a distal venous pressure from the vein by the at least one pressure sensor when fluid controlling device is in the on position, and measuring the distal venous pressure from the vein only by the at least one pressure sensor when the fluid controlling device is in the off position.

The fluid controlling device may be manually or automatically controllable. In one embodiment, the fluid controlling device includes a stopcock. In another embodiment, the fluid controlling device includes an intravascular line occlusion mechanism, which may be manual, automatic, or timed with cuff occlusion and cuff release.

In a further aspect, the invention relates to an apparatus for monitoring intravascular placement of a peripheral IV catheter. In one embodiment, the apparatus includes: a tubing with a first end and an opposite, second end, where in use, the first end is connected to a fluid source, and the second end is connected to the peripheral IV catheter that in turn is placed in a vein, a connector in fluid communication with the tubing, where the connector has first and second ports connected to the tubing and a narrow section formed therebetween, where the narrow section has an inner diameter smaller than that of the tubing, first and second pressure sensors in fluid communication with the tubing through the first and second ports of the connector, respectively, configured to measure fluid pressures therein, and a processor electrically coupled with the first and second pressure sensors for processing the measured fluid pressures by the first and second pressure sensors. When fluid passes from the fluid source to the IV catheter through the connector, a pressure drop of the fluid is generated at the narrow section, where the pressure drop is measureable by the first and second pressure sensors for calculating a pressure change rate dP/dt.

In one embodiment, each of the first and second pressure sensors includes a pressure transducer.

In one embodiment, the IV catheter is properly placed when the pressure change rate dP/dt is substantially constant or increases, and the IV catheter is not properly placed when the pressure change rate dP/dt is substantially absent or decreases.

The processor in one embodiment is associated with a circuit board of data acquisition and process.

In one embodiment, the apparatus further includes a display in communication with the processor for displaying the processed data. In a further embodiment, the display includes a graphic interface.

The apparatus in one embodiment further includes one or more additional pressure sensors in communication with the tubing, placed between the fluid source and the connector or between the connector and the vein for measuring fluid pressures therein.

In one aspect of the present invention, an apparatus for monitoring intravascular placement of a peripheral IV catheter includes: a tubing having a first end, an opposite, second end, and a narrow section formed therebetween, where in use, the first end is connected to a fluid source, and the second end is connected to the peripheral IV catheter that in turn is placed in a vein, and where the narrow section has an inner diameter smaller than that of other part of the tubing, first and second pressure sensors in fluid communication with the tubing, wherein one of the first and second pressure sensors is placed on a distal side of the narrow section to the IV catheter, and the other of the first and second pressure sensors is placed on a proximal side of the narrow section to the IV catheter, and a processor electrically coupled with the first and second pressure sensors for processing the measured fluid pressures by the first and second pressure sensors. When fluid flows from the fluid source to the IV catheter through the narrow section of the tubing, a pressure drop of the fluid is generated at the narrow section, and the pressure drop is measureable by the first and second pressure sensors for calculating a pressure change rate dP/dt.

The tubing in one embodiment includes a connector having a narrow portion and two ports on both sides of the narrow portions, where the narrow portion forms the narrow section of the tubing by having an inner diameter smaller than the diameter of the tubing, and the two ports are configured to be connected with the first and second pressure sensors, respectively.

In one embodiment, each of the first and second pressure sensors includes a pressure transducer.

In one embodiment, the IV catheter is properly placed when the pressure change rate dP/dt is substantially constant or increases, and the IV catheter is not properly placed when the pressure change rate dP/dt is substantially absent or decreases.

The processor in one embodiment is associated with a circuit board of data acquisition and process.

In one embodiment, the apparatus further includes a display in communication with the processor for displaying the processed data. In a further embodiment, the display includes a graphic interface.

The apparatus in one embodiment further includes one or more additional pressure sensors in communication with the tubing, placed between the fluid source and the connector or between the connector and the vein for measuring fluid pressures therein.

In another aspect of the present invention, a method for monitoring intravascular placement of a peripheral IV catheter includes: providing a tubing having a first end connected to a fluid source, and an opposite, second end connected to the peripheral IV catheter that in turn is placed in a vein, wherein the tubing has a narrow section between the first and second ends, where the narrow section has an inner diameter smaller than that of other part of the tubing, passing fluid from the fluid source to the vein through the tubing, measuring a pressure drop at the narrow section by first and second pressure sensors placed on both sides of the narrow section of the tubing, and determining whether the IV catheter is properly placed according to a pressure change rate dP/dt of the pressure drop.

In one embodiment, the IV catheter is properly placed when the pressure change rate dP/dt is substantially constant or increases, and the IV catheter is not properly placed when the pressure change rate dP/dt is substantially absent or decreases.

In one embodiment, the method further includes: displaying the determination results as to whether the IV catheter is properly placed on a display.

In yet another aspect of the present invention, a method for monitoring intravascular placement of a peripheral IV catheter includes: providing a tubing having a first end connected to a fluid source, and an opposite, second end connected to the peripheral IV catheter that in turn is placed in a vein, and a pressure sensor in fluid communication with the tubing, placed between the fluid source and the IV catheter; passing fluid from the fluid source to the vein through the tubing; measuring pressures of the fluid in the tubing by the pressure sensor; and determining an IV position or intravascular location of the IV catheter according to an algorithm in which the measured pressures are processed.

In one embodiment, the algorithm is based on analyzing waveforms of the measured pressures to include mean pressure, integral of waveform, variance, standard deviation, slope, sum of squares, correlation along a straight line, and changes or delta of any of these variables. The variables are measured, recorded, and compared over pre-determined time intervals to determine IV position.

The method may further include displaying the determined IV position or intravascular location of the IV catheter on a display.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1A:
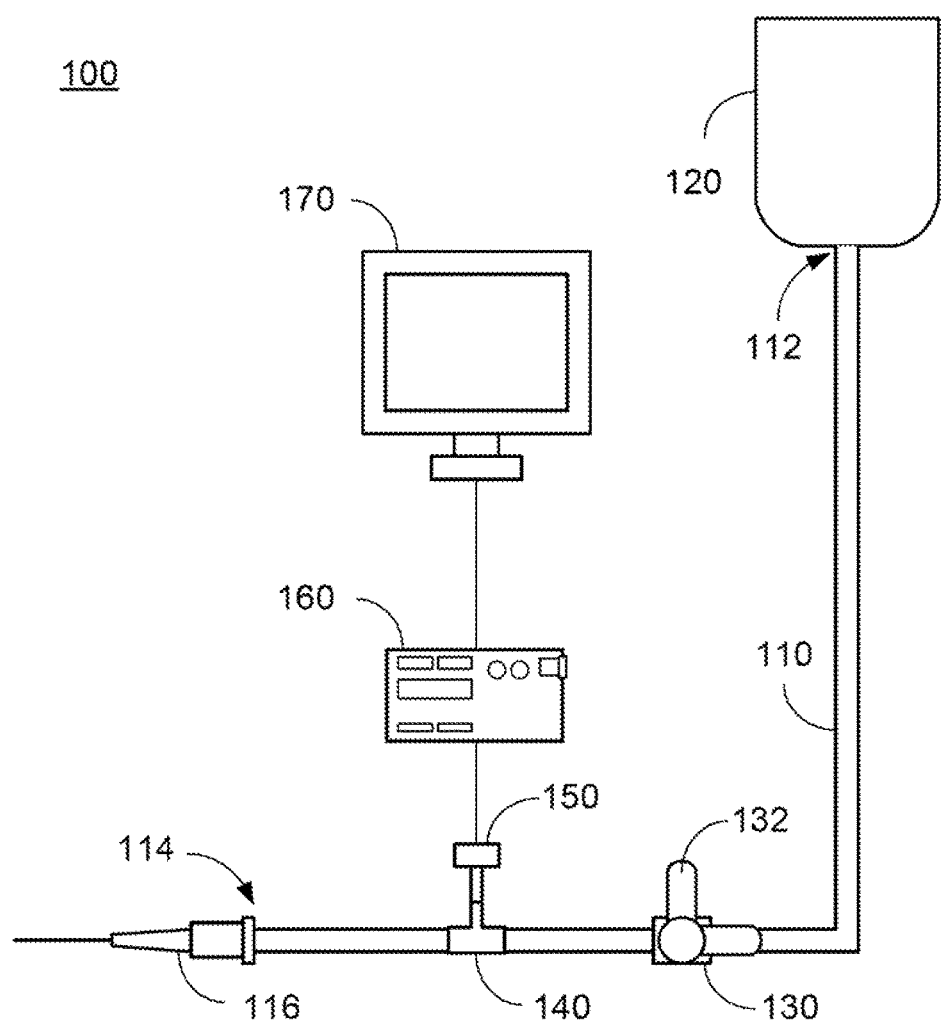
FIG. 1A shows schematically an apparatus for measuring peripheral venous pressure according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers, if any, indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the terms "comprising," "including," "having," "containing," "involving," and the like are to be understood to be open-ended, i.e., to mean including but not limited to.

As used herein, the terms "intravenous therapy", "intravenous tubing", the "intravenous" prefix, its abbreviation "IV" or the like generally refer to the infusion of liquid substances directly into a vein.

OVERVIEW OF THE INVENTION

The present invention discloses, among other things, apparatus and methods of utilizing IV tubing for measuring absolute PVP and CORRP in a non-invasive manner, and applications of the same in monitoring intravascular placement of a peripheral IV catheter. Further measurements of the venous waveform with or without fluids actively flowing from a fluid source are performed. An algorithm is utilized for determining proper or malpositioned IV catheters. This algorithm is based on analyzing the waveform to include mean pressure, integral of waveform, variance, standard deviation, slope, sum of squares, correlation along a straight line, and changes or delta of any of these variables. These variables are measured, recorded, and compared over predetermined time intervals to determine IV position. Based on these measurements, an alert or other signal is displayed to the operator regarding the IV position. This apparatus may communicate wirelessly so the alert can be displayed to the operator.

In one aspect of the present invention, an apparatus for measuring PVP includes a tubing having a first end connectable to a fluid source and a second end connectable to a vein, a fluid controlling device in fluid communication with the tubing, placed between the first and second ends of the tubing and configured to have an on position and an off position.

The apparatus also includes a port device in fluid communication with the tubing, placed between the fluid controlling device and the second end of the tubing, at least one pressure sensor in fluid communication with the tubing through the port device, configured to measure fluid pressures therein, and a processor electrically coupled with the at least one pressure sensor for processing the measured fluid pressures by the at least one pressure sensor.

In use, when the fluid controlling device is in the on position, fluid flow in the tubing is allowed to pass through the fluid controlling device, such that the at least one pressure sensor measures both a fluid pressure from the fluid source and a distal venous pressure from the vein, and when the fluid controlling device is in the off position, no fluid flow in the tubing is allowed to pass through the fluid controlling device, such that the at least one pressure sensor measures the distal venous pressure from the vein only.

In another aspect of the invention, an apparatus for measuring PVP includes a tubing having a first end connectable to a fluid source and a second end connectable to a vein, a fluid controlling device in fluid communication with the tubing, placed between the first and second ends of the tubing and configured to have an on position and an off position, and at least one pressure sensor in fluid communication with the tubing, placed between the fluid controlling device and the second end of tubing and configured to measure fluid pressures therein. In use, when the fluid controlling device is in the on position, fluid flow in the tubing is allowed to pass through the fluid controlling device, such that the at least one pressure sensor measures both a fluid pressure from the fluid source and a distal venous pressure from the vein, and when the fluid controlling device is in the off position, no fluid flow in the tubing is allowed to pass through the fluid controlling device, such that the at least one pressure sensor measures the distal venous pressure from the vein only.

In yet another aspect of the invention, a method of measuring PVP includes providing a tubing operably connected between a fluid source and a vein, a fluid controlling device in fluid communication with the tubing, placed in the tubing and configured to have an on position and an off position, and at least one pressure sensor in fluid communication with the tubing, placed between the fluid controlling device and the vein, selectively passing fluid from the fluid source to the vein through the tubing by the fluid controlling device, measuring both a fluid pressure from the fluid source and a distal venous pressure from the vein by the at least one pressure sensor when fluid controlling device is in the on position, and measuring the distal venous pressure from the vein only by the at least one pressure sensor when the fluid controlling device is in the off position.

In one aspect, the invention relates to an apparatus for monitoring intravascular placement of a peripheral IV catheter. The apparatus includes a tubing with a first end and an opposite, second end, where in use, the first end is connected to a fluid source, and the second end is connected to the peripheral IV catheter that in turn is placed in a vein. The apparatus also includes a connector in fluid communication with the tubing, where the connector has first and second ports connected to the tubing and a narrow section formed therebetween. The narrow section has an inner diameter smaller than that of the tubing. Further, the apparatus includes first and second pressure sensors in fluid communication with the tubing through the first and second ports of the connector, respectively, configured to measure fluid pressures therein, and a processor electrically coupled with the first and second pressure sensors for processing the measured fluid pressures by the first and second pressure sensors.

When fluid passes from the fluid source to the IV catheter through the connector, a pressure drop of the fluid is generated at the narrow section, where the pressure drop is measureable by the first and second pressure sensors for calculating a pressure change rate dP/dt.

In another aspect, the present invention relates to an apparatus for monitoring intravascular placement of a peripheral IV catheter. The apparatus in one embodiment includes a tubing having a first end, an opposite, second end, and a narrow section formed therebetween, where in use, the first end is connected to a fluid source, and the second end is connected to the peripheral IV catheter that in turn is placed in a vein, and where the narrow section has an inner diameter smaller than that of other part of the tubing.

The apparatus further has first and second pressure sensors in fluid communication with the tubing, where one of the first and second pressure sensors is placed on a distal side of the narrow section to the IV catheter, and the other of the first and second pressure sensors is placed on a proximal side of the narrow section to the IV catheter, and a processor electrically coupled with the first and second pressure sensors for processing the measured fluid pressures by the first and second pressure sensors. When fluid flows from the fluid source to the IV catheter through the narrow section of the tubing, a pressure drop of the fluid is generated at the narrow section, and the pressure drop is measureable by the first and second pressure sensors for calculating a pressure change rate dP/dt.

In a further aspect, the present invention relates to a method for monitoring intravascular placement of a peripheral IV catheter. In one embodiment, the method includes providing a tubing having a first end connected to a fluid source, and an opposite, second end connected to the peripheral IV catheter that in turn is placed in a vein. The tubing is configured to have a narrow section between the first and second ends. The narrow section has an inner diameter smaller than that of other part of the tubing.

The method also includes passing fluid from the fluid source to the vein through the tubing, measuring a pressure drop at the narrow section by first and second pressure sensors placed on both sides of the narrow section of the tubing, and determining whether the IV catheter is properly placed according to a pressure change rate dP/dt of the pressure drop.

In yet a further aspect, the present invention relates to a method for monitoring intravascular placement of a peripheral IV catheter. In one embodiment, the method includes, among other things, providing a tubing having a first end connected to a fluid source, and an opposite, second end connected to the peripheral IV catheter that in turn is placed in a vein, where the tubing may or may not have a narrow section between the first and second ends, and a pressure sensor in fluid communication with the tubing, placed between the fluid source and the IV catheter, passing fluid from the fluid source to the vein through the tubing, measuring pressures of the fluid in the tubing by the pressure sensor, and determining an IV position or intravascular location of the IV catheter according to an algorithm in which the measured pressures are processed. The algorithm is based on analyzing waveforms of the measured pressures to include mean pressure, integral of waveform, variance, standard deviation, slope, sum of squares, correlation along a straight line, and changes or delta of any of these variables. The variables are measured, recorded, and compared over pre-determined time intervals to determine IV position. Accordingly, these data do not require a pressure differential. Thus, only one pressure sensor is needed between the fluid source and the IV, and the data is collected while the fluid source is running thru the tubing into the IV.

These and other aspects of the present invention are more specifically described below.

IMPLEMENTATIONS AND EXAMPLES OF THE INVENTION

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

The description will be made as to the embodiments of the present invention in conjunction with the accompanying drawings in FIGS. 1-4. In accordance with the purposes of this disclosure, as embodied and broadly described herein, this disclosure, in one aspect, relates to compression and aggregation-resistant particles of crumpled soft sheets and methods of synthesizing same.

Referring to FIGS. 1A-1E, and particular FIG. 1A first, an apparatus for measuring the PVP is shown according to one embodiment of the present invention. The apparatus 100 is configured for measuring, among other things, absolute PVP and CORRP in a non-invasive manner. The apparatus 100 may be fixed or may be portable for the convenience of the medical environments where the system is utilized.

As shown in FIG. 1A, the apparatus 100 includes a tubing 110, a fluid source 120, a fluid controlling device 130, a port device 140, at least one pressure sensor 150, a circuit board 160, and a display 170.

The tubing 110 has a first end 112 and an opposite, second end 114. The first end 112 is connectable to the fluid source 120, such as an IV bag, a saline bag, or other bags or containers providing IV fluids. The second end 114 is connectable to a vein. In one embodiment, an IV catheter 116, which is a thin tube for inserting into a body, is provided for connecting the second end 114 of the tubing 110 to the vein.

Figure 1B:
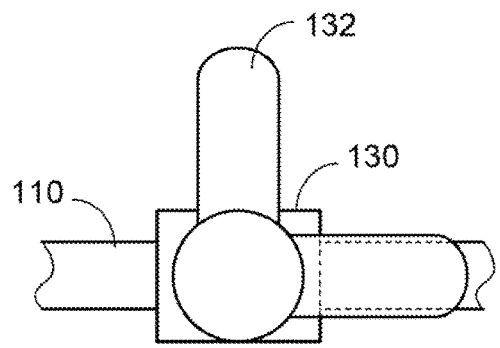
FIG. 1B shows an enlarged view of a stopcock of the fluid controlling device according to one embodiment of the present invention, where the fluid controlling device is in an on position.
Figure 1C:
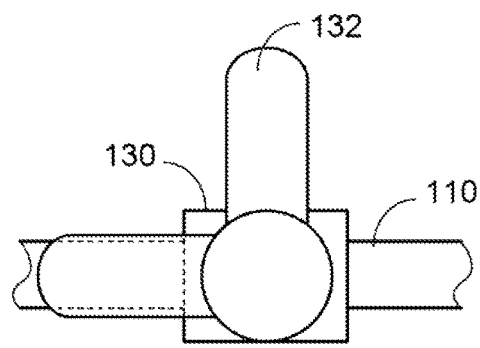
FIG. 1C shows an enlarged view of a stopcock of the fluid controlling device according to one embodiment of the present invention, where the fluid controlling device is in an off position.

The fluid controlling device 130 is in fluid communication with the tubing 110, and is placed between the first and second ends 112 and 114 of the tubing 110. The fluid controlling device 130 is configured to have an on position and an off position. The fluid controlling device 130 may be manually or automatically controllable. For example, the fluid controlling device 130 as shown in FIG. 1A includes a stopcock 132, which is shown in enlarged views in FIGS. 1B and 1C. By switching the stopcock 132, the fluid controlling device 130 can be manually controllable in the on position as shown in FIG. 1B, or in the off position as shown in FIG. 1C. When the fluid controlling device 130 is in the on position as shown in FIG. 1B, fluid flow in the tubing 110 is allowed to pass through the fluid controlling device 130. When a user controls the fluid controlling device 130 to be in the off position as shown in FIG. 1C, no fluid flow in the tubing 110 is allowed to pass through the fluid controlling device 130. In certain embodiments, the fluid controlling device 130 may include an intravascular line occlusion mechanism, which may be manual, automatic, or timed with cuff occlusion and cuff release.

The port device 140 is in fluid communication with the tubing 110, and is placed between the fluid controlling device 130 and the second end 114 of the tubing 110. The port device 140 may include a T-piece connector, which is shown in an enlarged view in FIG. 1D, or a Y-piece connector 118, which is shown in an enlarged view in FIG. 1E.

Figure 1D:
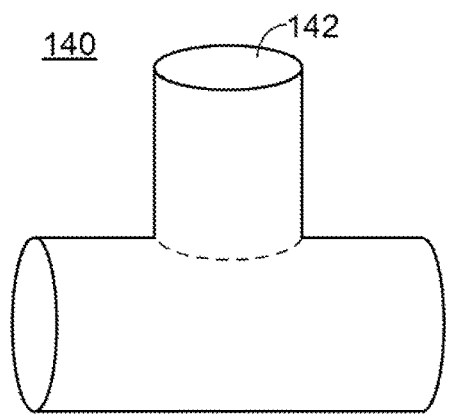
FIG. 1D shows an enlarged view of a T-piece connector according to one embodiment of the present invention.

The at least one pressure sensor 150 is in fluid communication with the tubing 110 through the port device 140, and is configured to measure fluid pressures therein. When the port device 140 includes the T-piece connector as shown in FIG. 1D, the at least one pressure sensor 150 is in fluid communication with the tubing 110 through the port 142 of the T-piece connector 140 for measuring the fluid pressures. The at least one pressure sensor may include a pressure transducer, a pressure transmitter, a pressure sensor, a pressure indicator, a piezometer, or any other types of pressure sensing or detecting devices or elements.

A processor is electrically coupled with the at least one pressure sensor 150 for processing the measured fluid pressures by the at least one pressure sensor 150. The measured fluid pressures may be processed by the processor for further data calculation and analysis, such as monitoring the fluid volume being provided in the IV therapy. In this exemplary embodiment shown in FIG. 1A, the processor is associated with the circuit board 160 of data acquisition and process, and the display 170 is in communication with the processor on the circuit board 160 for displaying the processed fluid pressures. The circuit board 160 may include standard computer input/output ports, such as USB ports, for further data process. The display 170 may include a graphic interface, such as a screen, or any other types of graphic information output devices or elements. Communication between the sensor and the display may be remotely transmitted via Bluetooth or radiofrequency mechanisms.

In operation, when the fluid controlling device 130 is in the on position, as shown in FIG. 1B, fluid flow in the tubing is allowed to pass through the fluid controlling device 130, such that the at least one pressure sensor 150 measures a pressure including a fluid pressure from the fluid source 120 and a distal venous pressure from the vein. Such measurement is done dynamically and continuously. Further, when the user operates or turns the stopcock 132 of the fluid controlling device 130 to the off position, as shown in FIG. 1C, no fluid flow in the tubing is allowed to pass through the fluid controlling device, such that the at least one pressure sensor measures the distal venous pressure, i.e., the baseline absolute peripheral venous pressure from the vein only. Following cuff-occlusion with a standard blood pressure cuff placed proximal to the peripheral IV, a variety of hemodynamic data, such as maximum PVP, rate of rise/slope of PVP, and rate of fall/slope of PVP following cuff release, among other parameters, may be obtained and analyzed.

Figure 1E:
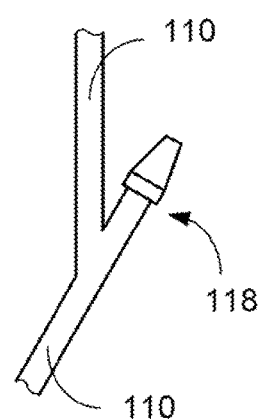
FIG. 1E shows an enlarged view of a Y-piece connector according to one embodiment of the present invention.

In some embodiments, the apparatus further includes one or more additional port device in fluid communication with the tubing 110. The one or more additional port device may be placed between the fluid source 120 and the port device 140 or between the port device 140 and the vein for measuring fluid pressures therein, such as differential flows from the fluid source 120 and the PVP from the vein, and for providing additional capability to input into and or output from the fluid inside the tubing 110. In other words, the at least one additional port device may be provided at any position between the first end 112 and the second end 114 of the tubing 110, and may be provided before or after the fluid controlling device 130. The one or more additional port device may be the T-piece connector as shown in FIG. 1D, or the Y-piece connector as shown in FIG. 1E.

Figure 2:
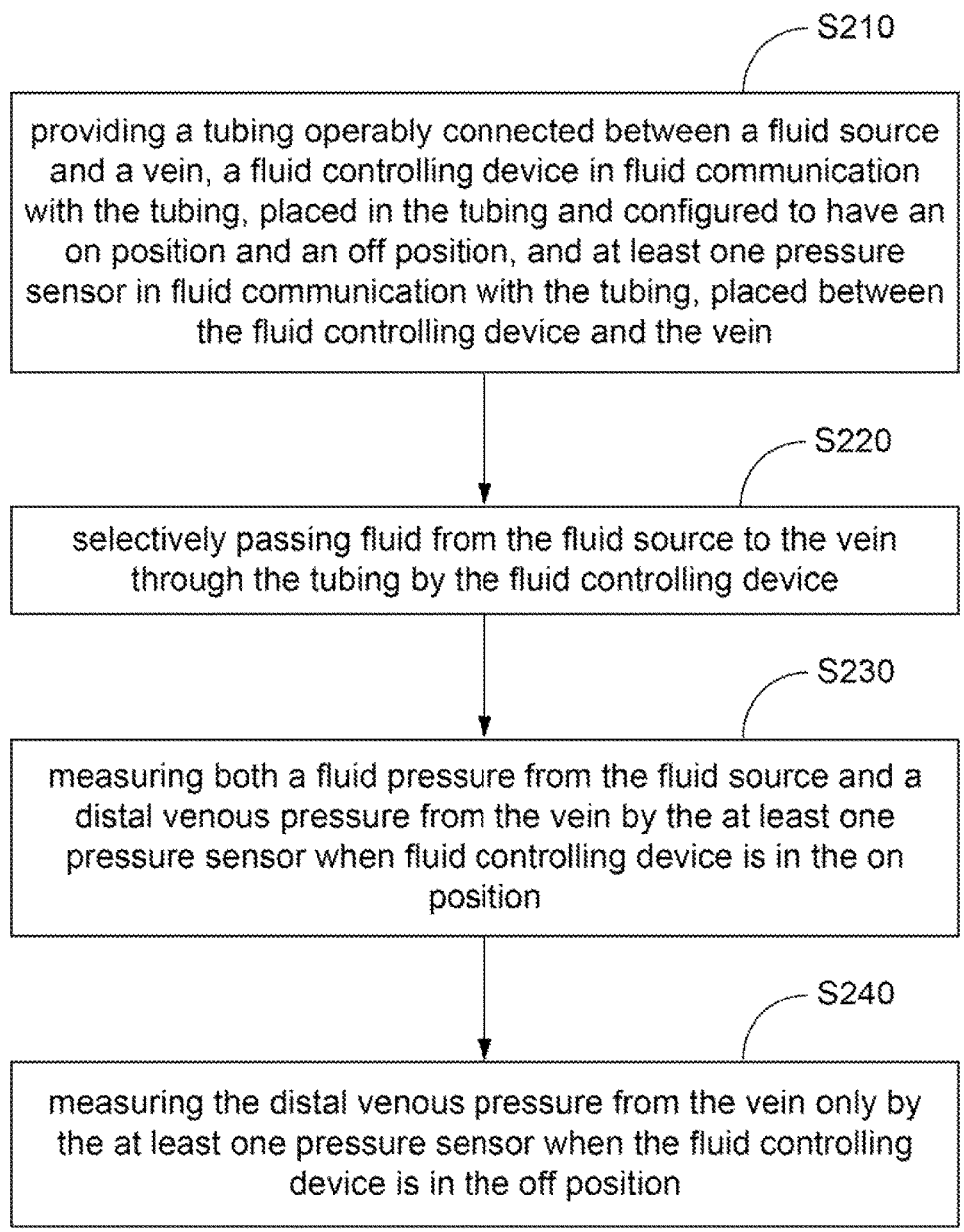
FIG. 2 shows a flowchart of measuring peripheral venous pressure according to one embodiment of the present invention.

FIG. 2 shows a flowchart of measuring PVP according to one embodiment of the present invention. Specifically, the method includes: providing a tubing operably connected between a fluid source and a vein, a fluid controlling device in fluid communication with the tubing, placed in the tubing and configured to have an on position and an off position, and at least one pressure sensor in fluid communication with the tubing, placed between the fluid controlling device and the vein (step S210), and then selectively passing fluid from the fluid source to the vein through the tubing by the fluid controlling device (step S220). When the fluid controlling device is in the on position, both a fluid pressure from the fluid source and a distal venous pressure from the vein are measured by the at least one pressure sensor (step S230), and when the fluid controlling device is in the off position, only the distal venous pressure from the vein is measured by the at least one pressure sensor (step S240). The fluid pressure and the distal venous pressure measured by the at least one pressure sensor may be processed by a processor and displayed on a display.

The advantages of the apparatus and method for measuring peripheral venous pressure over the currently available technologies include: eliminated need for invasive central venous access; reduced vascular and thoracic complications; reduced infection risk; point-of-care testing/portable and easy to use; applicable to military and civilian trauma situations; minimal training requirements; cost-effective; and more advance monitoring capabilities compared to existing absolute PVP pressure monitoring systems and methods, such as the technologies as disclosed in, for example, WO 2003/001973 and WO 2010/045556, respectively.

Figure 3A:
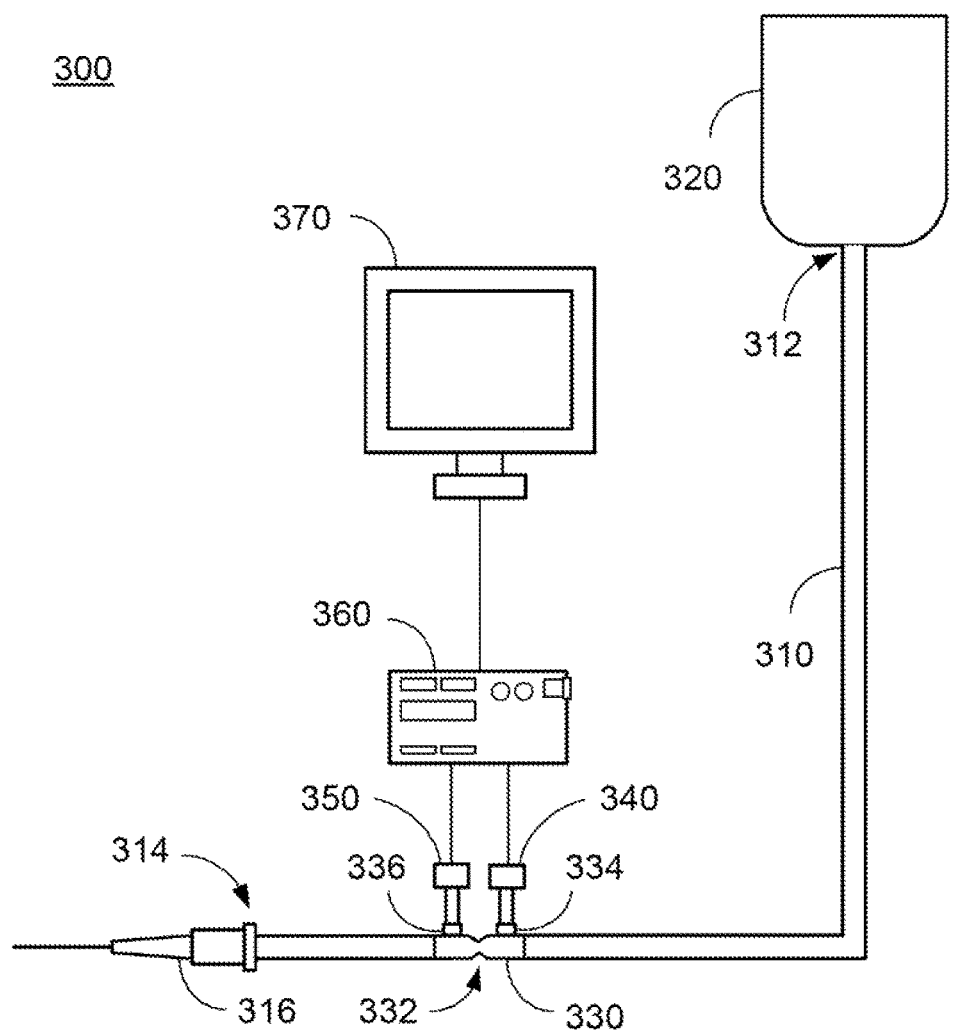
FIG. 3A shows schematically an apparatus for monitoring intravascular placement of a peripheral IV catheter according to one embodiment of the present invention.
Figure 3B:
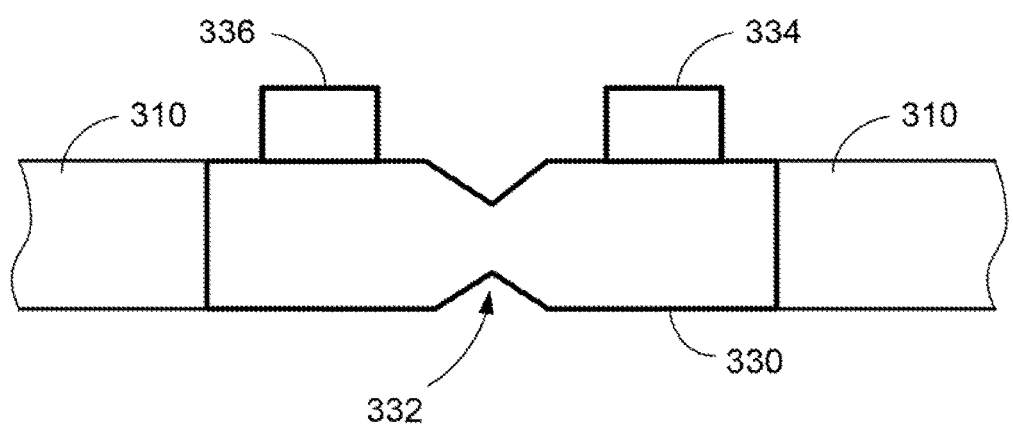
FIG. 3B shows an enlarged view of a connector according to one embodiment of the present invention.

Referring now to FIG. 3A, an apparatus for monitoring intravascular placement of a peripheral IV catheter is shown according to one embodiment of the present invention. The apparatus 300 is configured for detecting, among other things, proper intravascular catheter placement within the vein in a non-invasive manner, without the need for direct visualization of the IV site, such as within the operating arena where the IV is obscured by the sterile surgical drape. The apparatus 300 may be fixed or may be portable for the convenience of the medical environments where the system is utilized.

As shown in FIG. 3A, the apparatus 300 includes a tubing 310, a fluid source 320, a connector 330, first and second pressure sensors 340 and 350, a circuit board 160, and a display 170.

The tubing 310 has a first end 312 and an opposite, second end 314. The first end 312 is configured to be connected to the fluid source 320, such as an IV bag, a saline bag, or other bags or containers providing IV fluids. The second end 314 is connected to the peripheral IV catheter 316, which in turn is placed in a vein for performing IV therapy.

The tubing 310 has a narrow section between the first end 312 and the second end 314. The narrow section has an inner diameter smaller than that of other part of the tubing 310. In this embodiment, a connector 330, which includes the narrow section 332, is in fluid communication with the tubing 310. As shown in an enlarged view in FIG. 2B, the connector 330 has the narrow section 332 and first and second ports 334 and 336 on both sides of the narrow section 332, and the narrow section 332 has an inner diameter smaller than that of the tubing 310. The first and second ports 334 and 336 may be standard luer lock connecting ports.

The first and second pressure sensors 340 and 350 are in fluid communication with the tubing 310 through the first and second ports 334 and 336 of the connector 330, respectively, and are configured to measure fluid pressures therein. Thus, the two pressure sensors 340 and 350 would be positioned on both sides of the narrow section 332. In other words, the first pressure sensor 340 is positioned on a distal side of the narrow section 332 to the IV catheter 316, and the second pressure sensor 350 is positioned on a proximal side of the narrow section 332 to the IV catheter 316. Each of the first and second pressure sensors 340 and 350 may include a pressure transducer, a pressure transmitter, a pressure sender, a pressure indicator, a piezometer, or any other types of pressure sensing or detecting devices or elements.

A processor is electrically coupled with the first and second pressure sensors 340 and 350 for processing the measured fluid pressures by the first and second pressure sensors 340 and 350. In this embodiment, the processor is associated with the circuit board 360 of data acquisition and process, and a display 370 is in communication with the processor on the circuit board 360 for displaying the processed fluid pressures. The circuit board 360 may include standard computer input/output ports, such as USB ports, for further data analysis. The display 370 may include a graphic interface, such as a screen, or any other types of graphic information output devices. The display 370 may be color, waveform, or numerical to indicate IV position. Communication between the sensor and the display may be remotely transmitted via Bluetooth or radiofrequency mechanisms.

In operation, when fluid passes from the fluid source 320 to the IV catheter 316 through the connector 330, a pressure drop of the fluid is generated at the narrow section 332 due to the smaller inner diameter of the narrow section 332. Thus, the first pressure sensor 340 measures the higher-pressure flow before the narrow section 332, and the second pressure sensor 350 measures the lower-pressure flow after the narrow section 332. In other words, the pressure drop is measureable by the first and second pressure sensors 340 and 350. The pressure drop can be used for calculating by slope and derivative of rate of fall of pressure, i.e., a pressure change rate dP/dt.

In a low pressure venous system, measurements in patients with a properly placed IV catheter 316 will display a pressure drop with a constant or increasing pressure change rate dP/dt. In contrast, if the IV catheter 316 is malpositioned or misplaced, such as in the subcutaneous tissue, there will be a decreased or absent pressure change rate dP/dt, which can provide a reading or signal to the user or operator for correcting the misplacement. In other words, the IV catheter 316 is properly placed when the pressure change rate dP/dt is substantially constant or increases, and the IV catheter 316 is not properly placed when the pressure change rate dP/dt is substantially absent or decreases.

In one embodiment, the apparatus 300 may further include one or more additional port device in fluid communication with the tubing 310. The one or more additional port device may be placed between the fluid source 320 and the connector 330 or between the connector 330 and the vein for measuring fluid pressures therein.

Figure 4:
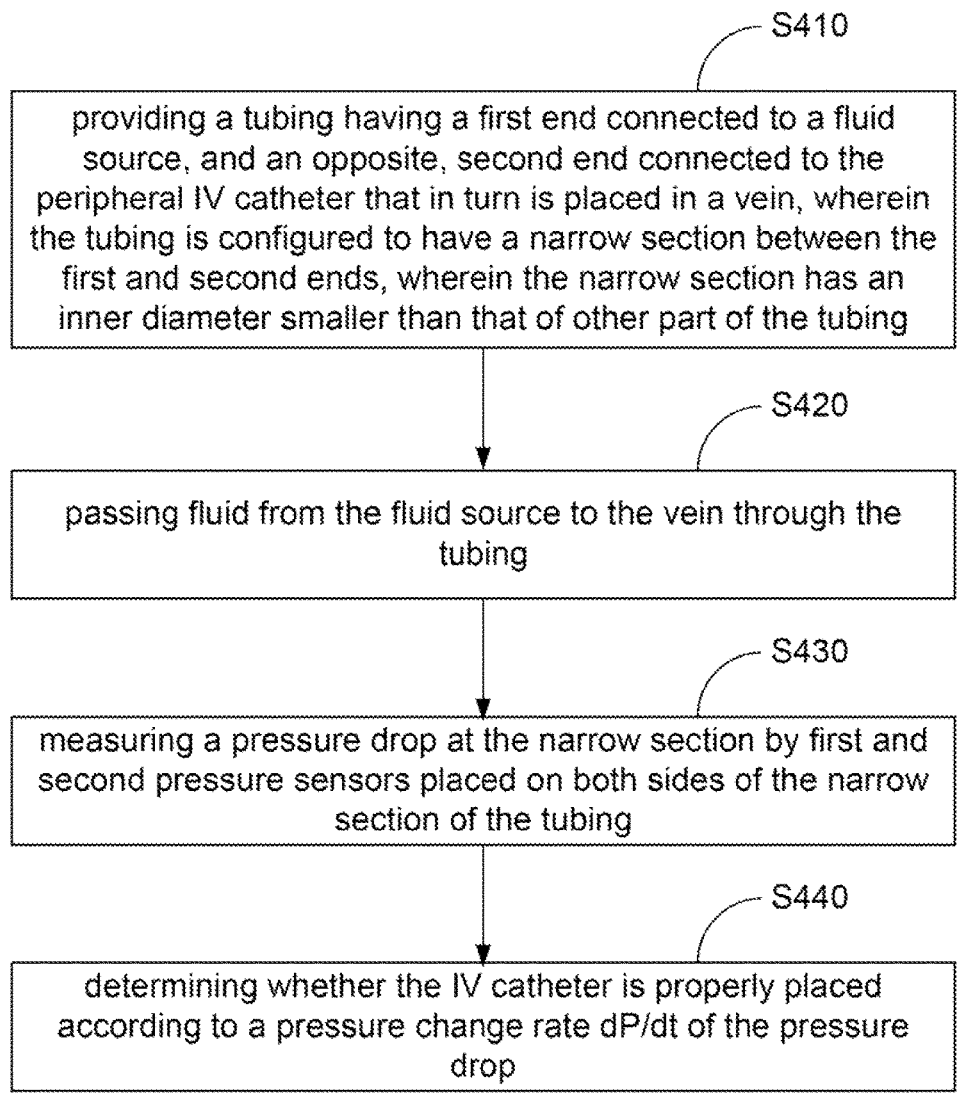
FIG. 4 shows a flowchart of monitoring intravascular placement of a peripheral IV catheter according to one embodiment of the present invention.

FIG. 4 shows a flowchart of monitoring intravascular placement of a peripheral IV catheter according to one embodiment of the present invention. Specifically, the method includes: providing a tubing having a first end connected to a fluid source, and an opposite, second end connected to the peripheral IV catheter that in turn is placed in a vein, wherein the tubing is configured to have a narrow section between the first and second ends, wherein the narrow section has an inner diameter smaller than that of other part of the tubing (step S410), and passing fluid from the fluid source to the vein through the tubing (step S420). A pressure drop at the narrow section is then measured by first and second pressure sensors placed on both sides of the narrow section of the tubing (step S430), and then whether the IV catheter is properly placed is determined according to a pressure change rate dP/dt of the pressure drop (step S440). In one embodiment, the determination results as to whether the IV catheter is properly placed may be displayed on a display.

In one aspect, the present invention also relates to a method that utilizes a single pressure sensors/transducer without needing a pressure differential or controlling fluid rate/turning fluids off, etc. to monitor intravascular placement of a peripheral IV catheter. Practically, the pressure sensors/transducer is still placed between the fluid source and the IV. As such, measured pressure and waveform data can be analyzed/processed while the fluids are actively running into the IV.

In one embodiment, the method includes, among other things, providing a tubing having a first end connected to a fluid source, and an opposite, second end connected to the peripheral IV catheter that in turn is placed in a vein, where the tubing may or may not have a narrow section between the first and second ends, and a pressure sensor in fluid communication with the tubing, placed between the fluid source and the IV catheter, passing fluid from the fluid source to the vein through the tubing, measuring pressures of the fluid in the tubing by the pressure sensor, and determining an IV position or intravascular location of the IV catheter according to an algorithm in which the measured pressures are processed.

The algorithm is based on analyzing waveforms of the measured pressures to include mean pressure, integral of waveform, variance, standard deviation, slope, sum of squares, correlation along a straight line, and changes or delta of any of these variables. The variables are measured, recorded, and compared over pre-determined time intervals to determine IV position. Accordingly, these data do not require a pressure differential. Thus, only one pressure sensor is needed between the fluid source and the IV, and the data is collected while the fluid source is running thru the tubing into the IV.

The method may further include displaying the determined IV position or intravascular location of the IV catheter on a display. The display may be color, waveform, or numerical to indicate IV position. Communication between the sensor and the display module may be remotely transmitted via Bluetooth or radiofrequency mechanisms.

The advantages of the apparatus and method for monitoring intravascular placement of a peripheral IV catheter according to various embodiments of the present invention include a measureable pressure drop resulted in the narrow section between the pressure sensors, and continuous monitoring across pressure drop, even with intravascular fluids running. An algorithm based on statistical analysis of the waveform and numerical data to include mean and absolute pressure, integral, variance, standard deviation, slope, sum of squares, correlation along a straight line, and changes or delta of any of these variables. The result may be displayed graphically, numerically, or color coded for proper IV placement. For example, a display of green color may be used for proper intravascular placement, and a red sign may be used for checking for malpositioned or occluded intravascular catheter.

The apparatuses and methods as disclosed in the aforementioned embodiments are capable of being utilized in potential connections within the same system. In such a combined system, a fluid controlling device such as a stopcock is utilized to operate the apparatus with an on position and an off position to statistically analyze absolute and changes in venous pressures, venous pressure waveform or the combination of these waveforms with fluids actively flowing through. A high mean pressure (>40 mmHg) or change in pressure for example may alert to IV catheter kinking, occlusion, misplacement or malpositioning. Simultaneous or combined measurements of the fluid source and the venous pressure waveform from the IV may determine without the need for the pressure drop across a narrow section, but with measurement of a single area or multiple areas along the tubing.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. For example, multiple probes may be utilized at the same time to practice the present invention. Accordingly, the scope of the present invention is defined by the appended claims rather than the foregoing description and the exemplary embodiments described therein.

LIST OF REFERENCES

[1]. Becker L B, Weisfeldt M L, Weil M H, et al.: The PULSE initiative: scientific priorities and strategic planning for resuscitation research and life saving therapies. Circulation 105:2562-2570, 2002.

[2]. Convertino V A, Ryan K L, Rickards C A, et al.: Physiological and medical monitoring for en route care of combat casualties. J Trauma 64:S342-353, 2008.

[3]. Convertino V A and Ryan K L: Identifying physiological measurements for medical monitoring: implications for autonomous health care in austere environments, J Gravit Physiol 14:P39-42, 2007.

[4]. Desebbe O, Boucau C, Farhat F, et al.: The ability of pleth variability index to predict the hemodynamic effects of positive end-expiratory pressure in mechanically ventilated patients under general anesthesia. Anesth Analg 110:792-798, 2010,

[5]. Amar D, Melendez J A, Zhang H, et al.: Correlation of peripheral venous pressure and central venous pressure in surgical patients. J Cardiothorac Vasc Anesth 15:40-43, 2001.

[6]. Munis J R, Bhatia S and Lozada L J: Peripheral venous pressure as a hemodynamic variable in neurosurgical patients. Anesth Analg 92:172-179, 2001.

[7]. Wolf W M, Snyder C L, Porter J, et al.: Cuff-occluded rate of rise of peripheral venous pressure: a new, highly sensitive technique for monitoring blood volume status during hemorrhage and resuscitation. Surgery 101:304-309, 1987.

[8]. Soller B R, Yang Y, Soyemi O O, et al.: Noninvasively determined muscle oxygen saturation is an early indicator of central hypovolemia in humans. J Appl Physiol 104: 475-481, 2008.

What is claimed is:

1. A method for monitoring intravascular placement of a peripheral intravenous (IV) catheter, comprising:
(a) providing a tubing having a first end connected to a fluid source, and an opposite, second end connected to the peripheral IV catheter that in turn is placed in a vein, only one pressure sensor in fluid communication with the tubing, placed between the fluid source and the peripheral IV catheter, and a fluid controlling device in fluid communication with the tubing, placed in the tubing and between the fluid source and only one pressure sensor, and configured to have an on position and an off position, such that when the fluid controlling device is in the on position, fluid in the tubing is allowed to pass through the fluid controlling device, and when the fluid controlling device is in the off position, no fluid in the tubing is allowed to pass through the fluid controlling device;
(b) selectively passing fluid from the fluid source to the vein through the tubing by the fluid controlling device;
(c) measuring a pressure including a fluid pressure from the fluid source and a distal venous pressure from the vein by the only one pressure sensor when the fluid controlling device is in the on position; and measuring only the distal venous pressure from the vein by the only one pressure sensor when the fluid controlling device is in the off position;
(d) generating waveforms from the measured pressures; and
(e) determining an IV position or intravascular location of the peripheral IV catheter from the waveforms, wherein the determination of the IV position or intravascular location of the peripheral IV catheter from the waveforms is performed by analyzing a plurality of variables of the waveforms according to an algorithm, such that a pressure differential is not used in determining the IV position or intravascular location of the peripheral IV catheter.

2. The method of claim 1, wherein the variables of the waveforms include mean pressure, integral of waveform, variance, standard deviation, slope, sum of squares, correlation along a straight line, and changes or delta of any of these variables.

3. The method of claim 2, wherein the algorithm is performed by a step of measuring, recording and comparing the variables of the waveforms over pre-determined time intervals to determine the IV position.

4. The method of claim 1, further comprising displaying the determined IV position or intravascular location of the peripheral IV catheter on a display.

5. The method of claim 4, wherein communication between the pressure sensor and the display is remotely transmitted via wireless or radiofrequency mechanisms.

6. The method of claim 1, wherein the determination of the IV position or intravascular location of the peripheral IV catheter from the waveforms comprises:
determining whether the peripheral IV catheter is properly placed in the vein.

7. The method of claim 1, wherein the measured pressures are distal venous pressures from the vein.

* * * * *